United States Patent

Steele et al.

[11] Patent Number: 5,816,910
[45] Date of Patent: Oct. 6, 1998

[54] INFANT SOOTHER APPARATUS

[76] Inventors: Richard G. Steele; Margaret C. Steele, both of 1836 Owens Ave., Albany, Ga. 31705-1070

[21] Appl. No.: 853,246

[22] Filed: May 9, 1997

[51] Int. Cl.[6] ................................................ A61M 21/00
[52] U.S. Cl. ............................... 454/370; 600/28; 601/47
[58] Field of Search .................................... 454/338, 370; 600/28; 601/47

[56] References Cited

U.S. PATENT DOCUMENTS

| | | | |
|---|---|---|---|
| 729,317 | 5/1903 | Fleetwood | 601/47 X |
| 2,830,578 | 4/1958 | Groff | 601/47 |
| 3,094,972 | 6/1963 | Leavenworth | 600/28 X |
| 5,063,912 | 11/1991 | Hughes | 600/28 X |
| 5,464,381 | 11/1995 | Wilson | 601/49 |

*Primary Examiner*—Harold Joyce
*Attorney, Agent, or Firm*—Martin Sachs

[57] ABSTRACT

A portable apparatus for soothing infants to enable them to fall asleep utilizes a portable housing having a cylindrically-shaped intake and exhaust opening coupled by a hollow cylindrical tube into which is located a miniature motor disposed proximate the intake opening with fan blades affixed on the rotating motor shaft that provides an air flow over a plurality of flexible members disposed proximate the exhaust opening. A control arrangement, coupled to a battery power source, is disposed within the housing for controlling the amount of forced air flowing out of the exhaust opening so that the tone or the sounds emanating from the apparatus can be controlled.

12 Claims, 2 Drawing Sheets

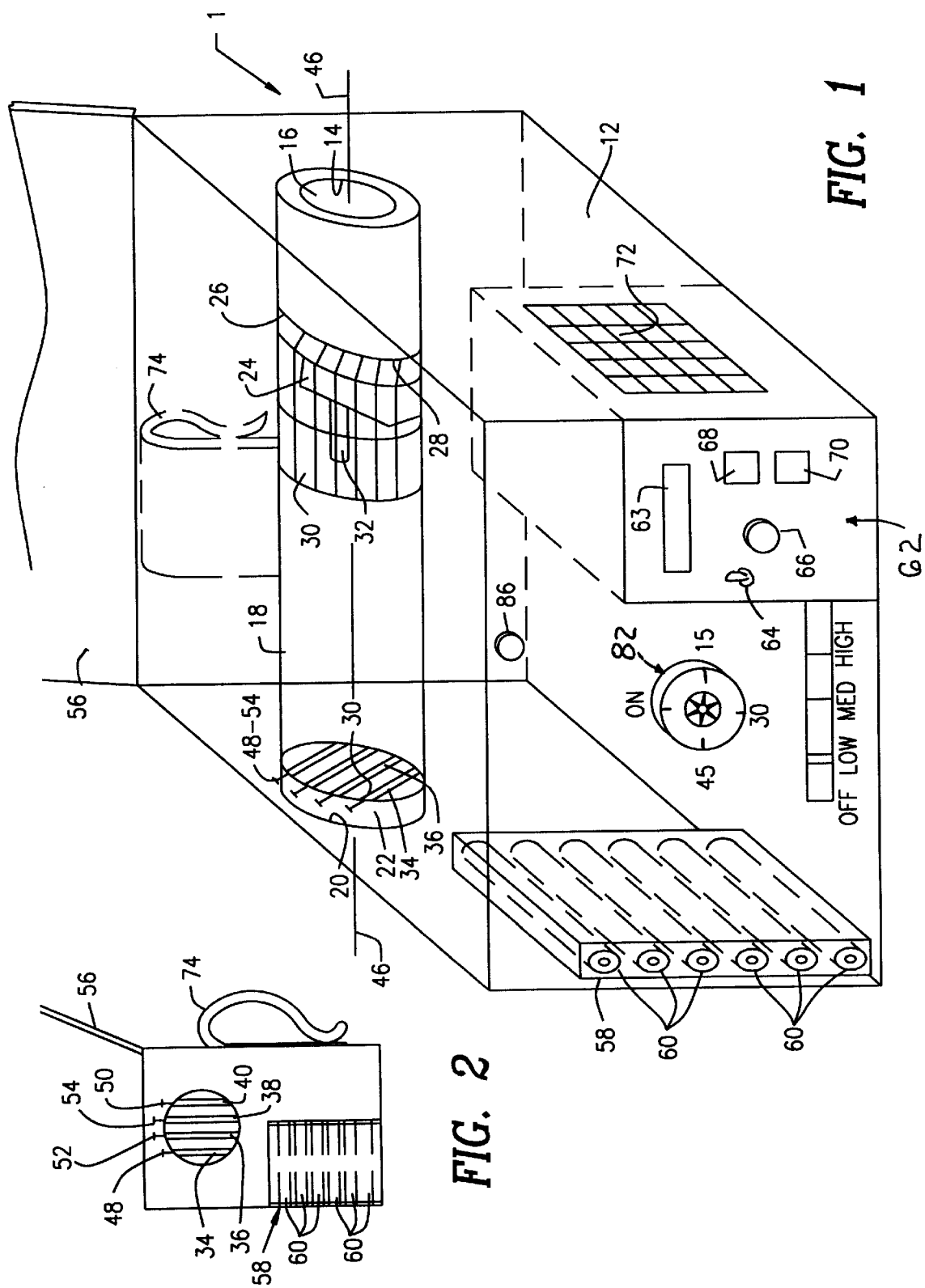

INFANT SOOTHER APPARATUS

BACKGROUND OF THE INVENTION

1. Field of the Invention

The present invention relates to an apparatus for providing a soothing noise level to enable infants to readily fall asleep.

2. Discussion of the Relevant Art

Typical of devices, which provide a soothing noise to improve the work area of individuals is disclosed in U.S. Pat. No. 5,360,469 which issued to Baron, et. al. on Nov. 1, 1994. The apparatus disclosed therein is designed to provide "pink noise," which is soothing to an individual and overcomes the surrounding noise so that an individual may work more efficiently.

Other devices, known in the art, are utilized to drown out or absorb surrounding noise so that the ambient is reduced to a tolerable and not an irritating noise level.

The present invention overcomes the shortcomings found in the prior art by providing a soothing noise ambient so that newborn babies will readily fall to sleep, giving parents a chance to sleep and thereby be rejuvenated for the next day.

"White noise" is sound that overcomes and naturally wipes out background noise. "Pink noise" is soothing background noise. Two examples of "pink noise" are a persons heart beat and noises produced by motor driven electrical appliances. Tests have shown that "pink noise" will soothe crying babies so that they are able to sleep without the aid of a bottle or pacifier. It has been found that several recorded tapes that play human hearts beating, soft lullablys and "pink noise" mixed therewith is soothing to infants. Moreover, devices that actually reproduce these soothing sounds are more effective than a recording of the sounds.

Therefore, it is a object of the present invention to provide an infant soother apparatus that is inexpensive and affordable and usable both in the nursery and in an automobile.

It is another object of the present invention to provide an infant soother apparatus that combines the sounds of a motor with sounds of flexible members waving in the breeze caused by an miniature motor.

It is yet another object of the present invention to provide an infant soother apparatus that allows the user thereof to couple recorded sounds together with sounds of a running motor and/or vibrating flexible members.

SUMMARY OF THE PRESENT INVENTION

The present invention overcomes the shortcomings found in the prior art by providing an infant soother apparatus that includes a portable housing, which has disposed therein a cylindrically-shaped intake and exhaust openings coupled by a hollow cylindrical tube, which has a longitudinal axis and a plurality of relatively narrow flexible members disposed proximate the exhaust opening, transverse to the longitudinal axis. A miniature motor is disposed proximate the intake opening within the housing tube portion and includes fan blades affixed on the rotating shaft of the miniature motor and is disposed about the motor circumference. A control assembly, disposed within the housing, controls the speed of the motor and the amount of forced air flowing out of the exhaust opening. Also included is a battery power source coupled to the controls for controlling the motor speed and the air flow, thereby selectively changing the amount of "pink noise" emanating from the apparatus.

The foregoing and other objects and advantages will appear from the description to follow. In the description, reference is made to the accompanying drawing, which forms a part hereof, and in which is shown by way of illustration a specific embodiment in which the invention may be practiced. This embodiment will be described in sufficient detail to enable those skilled in the art to practice the invention. It is to be understood that other embodiments may be utilized and that structural changes may be made without departing from the scope of the invention. The following detailed description is, therefore, not to be taken in a limiting sense and the scope of the present invention is best defined by the appended claims.

BRIEF DESCRIPTION OF THE DRAWINGS

In order that the invention may be more fully understood, it will now be described, by way of example, with reference to the accompanying drawing in which:

FIG. 1 is a pictorial representation in perspective of an infant soother apparatus, according to the principles of the present invention;

FIG. 2 is an end view in elevational of the apparatus shown in FIG. 1;

DESCRIPTION OF THE PREFERRED EMBODIMENT

Figure 3:
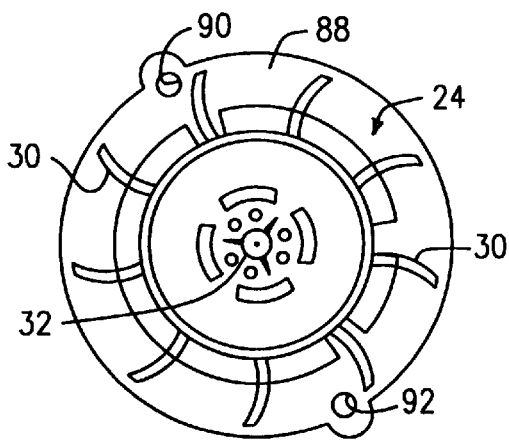
FIG. 3 is a top plan view of a miniature DC motor showing the fan blades disposed thereon.

Referring now to the figures, and in particular FIGS. 1 and 2, there is shown an infant soother apparatus 10 that includes a portable housing 12, which has a cylindrically-shaped opening 14 disposed therein, that may be covered with a filter membrane 16, connected by a hollow cylindrically-shaped member 18 to an exhaust opening 20, which also may be covered by a filter membrane 22.

A miniature D.C. motor 24 is disposed within the hollow cylinder 18 and is held in place by utilizing two nuts and bolts, not shown, to two internally extending tabs 26 and 28. A fan blade 30 is affixed on the shaft 32 of the motor 24. (See FIG. 3) Proximate the exhaust opening 20 is a plurality of relatively narrow flexible members 34, 36, 38 and 40 disposed transverse to the longitudinal axis 46 of the hollow cylinder member 18. The flexible members 34, 36, 38 and 40 have one end thereof affixed within the hollow cylinder and are stretched across the hollow cylinder member 18 where they are held by a clamping device 48, 50, 52 and 54 so that their tension may be adjusted by pulling on the clamping device, adjusting the tautness of each of the flexible members 34, 36, 38 and 40 as desired. Access to the clamping devices 48, 50, 52 and 54 may be had by lifting one end of the hinged cover 56 from the top of the housing 12.

The housing 12 also includes a battery compartment, which has contained therein a plurality of batteries 60 used to supply power to the motor 24 and a cassette recorder 62 disposed within the housing 12, which includes its own ON/OFF switch 64, volume control 66, eject button 68 and play button 70 and an internal speaker 72. Also included on the housing 12 is a mounting clamp 74, which may include a tamper mechanism, not shown.

The controls for operating the motor 24 are seen to include a timer switch 82, which permits the fan motor to be either locked in the "ON" position or may be set to any time up to one hour. A speed control switch 84 permits the setting of the motor to low, medium or high. If the batteries 60 should be drained of power and have a reduced voltage, a low battery indicating (LED) 86 will light, thereby telling the user of the apparatus that it is time to either change the batteries or utilize a battery charging device, not shown.

Referring now to FIG. 3, which is top plan view of the motor 24 with the fan blades 30 disposed thereon. The base of the motor housing 88 is seen to include two mounting holes 90 and 92. Mounting screws, not shown, are inserted through the mounting holes 90 and 92 and then are inserted through the internally extending tabs 26 and 28, which are provided with mating holes, not shown.

Figure 4:
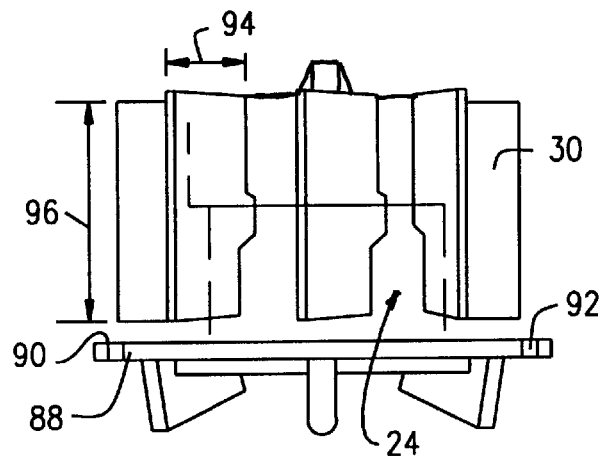
FIG. 4 is a end view in elevational of the fan blades disposed in the motor as shown in FIG. 3

A side view in elevation of the motor 24, with the fan blades 30 disposed thereon, is shown in FIG. 4. The fan blades 30, preferably have a radially extended length 94 of about 0.5 inches and an longitudinally extending length 96 of about 2.5 inches with a portion of the longitudinal length 96 being free to flex when the motor is rotated, thereby providing audible sounds, which will enter the surrounding area of the infant soother apparatus 10.

Figure 5:
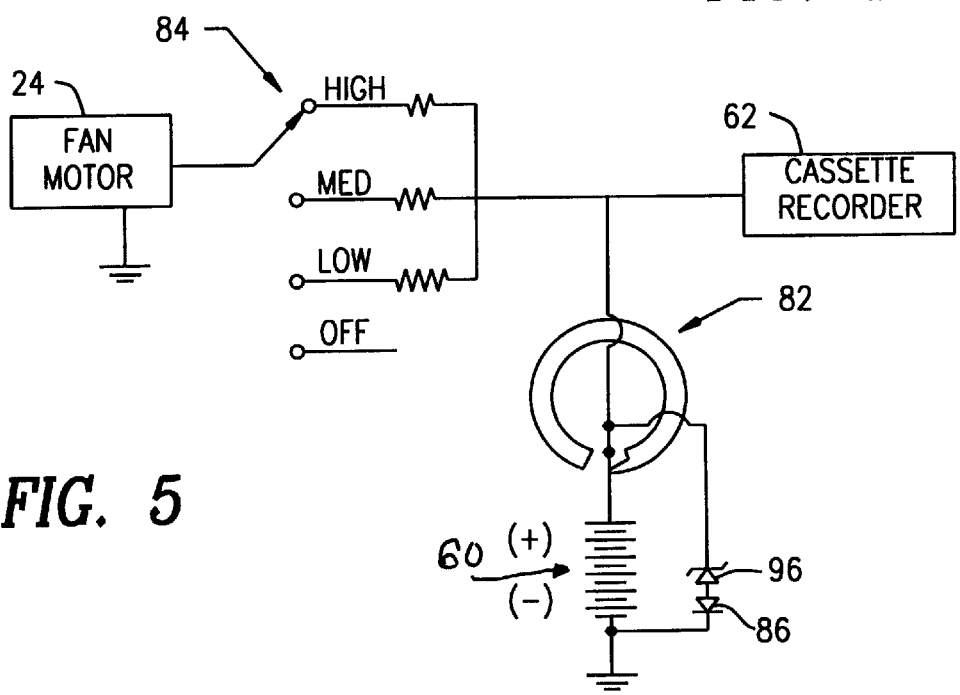
FIG. 5 is a schematic circuit diagram, showing the operating controls of the infant soother apparatus.

Referring now to FIG. 5 which shows the control circuitry for the infant soother apparatus 10. The fan motor is connected to a speed control switch 84, which has four positions, which are an OFF, LOW, MEDIUM and HIGH position, that may be selected by the operator of the apparatus. Each position has a different value resistor in series therewith, the other end of which is connected to the voltage source through a rotating timer switch 82. The cassette player 62 is also connected to the rotary timer control switch to the source of voltage 60. The rotary timer control switch allows for a hold position and a timer that may be set as needed. An ON/OFF switch is also provided. Across the batteries 60 is placed an LED 86, which will indicate when the apparatus 10 has been turned on and the voltage of the battery 60 is sufficient to exceeed the breakover voltage of the zener diode 96, thereby allowing the LED 86 to conduct showing that the equipment is operating satisfactory. As the battery voltage decreases and goes below the voltage of the zener diode 96, the LED will be unable to conduct, thereby telling the owner thereof that it is time to replace the batteries or alternatively use a battery recharging system, not shown.

It will be understood that various changes in the details, materials, arrangements of parts and operating conditions which have been herein described and illustrated in order to explain the nature of the invention may be made, by those skilled in the art, within the principles and scope of the instant invention.

Hereinbefore has been disclosed an infant soother apparatus 10, which is designed so that the operating thereof may utilize the sounds provided by the apparatus itself, with varying speeds of the motor or alternatively may include particular sounds that are soothing to an infant by utilizing the cassette recorder 62 in combination therewith.

Having thus set forth the nature of the invention, what is claimed is:

1. An infant soother apparatus comprising:
   A. a portable housing means, said housing means including;
      a) a cylindrically-shaped intake opening and a cylindrically-shaped exhaust opening coupled by a hollow cylindrical tube portion having a longitudinal axis, and
      b) a plurality of relatively narrow flexible members disposed proximate said exhaust opening transverse to said longitudinal axis;
   B. a miniature motor disposed proximate said intake opening within said housing hollow cylindrical tube portion, said motor including,
      a) fan blades affixed on the rotating shaft of said miniature motor for forcing air over said plurality of flexible members;
   C. control means, disposed within said housing, for controlling the speed of said motor and the amount of forced air flowing out of said exhaust opening; and
   D. a power source, coupled to said control means and said motor, disposed within said portable housing means;
   wherein controlling the speed of said fan blades changes the sounds emanating from said motor and said plurality of flexible members, thereby changing the sounds emanating from said infant soother apparatus.

2. An infant soother apparatus according to claim 1, wherein said cylindrically-shaped intake opening and said cylindrically-shaped exhaust opening are provided with filter means to remove dust from the air.

3. An infant soother apparatus according to claim 1, wherein said power source is a re-chargeable battery pack and converter that provides an output of 60 hertz to operate said motor.

4. An infant soother apparatus according to claim 1, wherein said fan blades are approximately 2.0 to 3.0 inches long and approximately 0.4 to 0.6 inches wide and extend longitudinally along the longitudinal axis of said hollow tube cylindrical portion.

5. An infant soother apparatus according to claim 1, wherein said fan blades are preferably 2.5 inches long and 0.5 inches wide and extend longitudinally along the longitudinal axis of said hollow tube cylindrical portion.

6. An infant soother apparatus according to claim 1, further including means for adjusting the tautness of said plurality of flexible members to vary the sounds emanating therefrom.

7. An infant soother apparatus according to claim 1, further including an audio reproducing system for playing pre-recorded sounds disposed in said housing means and coupled to said control means and said power source.

8. An infant soother apparatus according to claim 7, wherein said control means further includes means for operating said audio reproducing system.

9. An infant soother apparatus comprising:
   A. a portable housing means, said housing means including;
      a) a cylindrically-shaped intake opening and a cylindrically-shaped exhaust opening coupled by a hollow cylindrical tube portion having a longitudinal axis,
      b) a plurality of relatively narrow flexible members disposed proximate said exhaust opening transverse to said longitudinal axis, and
      c) an audio reproducing system for playing pre-recorded sounds disposed in said housing means and coupled to said control means;
   B. a miniature motor disposed proximate said intake opening disposed within said housing hollow cylindrical tube portion, said motor having,
      a) fan blades affixed on the rotating shaft of said miniature motor for forcing air over said plurality of flexible members, said fan blades being preferably 2.5 inches long and 0.5 inches wide extending longitudinally along the longitudinal axis of said hollow tube cylindrical portion; and
   C. control means, disposed within said housing and coupled to said motor, for controlling the speed of said motor and the amount of forced air flowing out of said exhaust opening; and D. a power source, coupled to said motor and said control means, disposed within said portable housing means;

wherein controlling the speed of said fan blades changes the sounds emanating from said motor and said plurality of flexible members, thereby changing the sounds emanating from said infant soother apparatus.

10. An infant soother apparatus according to claim 9, further including means for adjusting the tautness of said plurality of flexible members to vary the sounds emanating therefrom.

11. An infant soother apparatus according to claim 9, wherein said portable housing means includes a spring clip means for affixing said housing means to a vertical surface.

12. An infant soother apparatus according to claim 1, wherein said portable housing means includes a spring clip means for affixing said housing means to a vertical surface.

* * * * *